United States Patent [19]

Kelly

[11] Patent Number: 4,533,642
[45] Date of Patent: Aug. 6, 1985

[54] METAL ANALYSIS FOR ACID-SOLUBLE ELEMENTS

[75] Inventor: John H. Kelly, Burlington, Canada

[73] Assignee: Stelco Inc., Hamilton, Canada

[21] Appl. No.: 372,079

[22] Filed: Apr. 26, 1982

[30] Foreign Application Priority Data

Apr. 2, 1982 [CA] Canada .................................. 400398

[51] Int. Cl.³ ............................................ G01N 33/20
[52] U.S. Cl. ........................................ 436/78; 436/73
[58] Field of Search ........................ 436/78, 164, 175; 204/15, 140

[56] References Cited

U.S. PATENT DOCUMENTS 3,794,569 2/1974 Kawai et al. ........................ 204/1 T
3,901,786 8/1975 Wheelwright ...................... 204/140
4,111,776 9/1978 Mansfield ............................ 204/1 T

FOREIGN PATENT DOCUMENTS 772768 11/1967 Canada .
2527555 1/1976 Fed. Rep. of Germany ........ 436/78
48-55791 8/1973 Japan ..................................... 436/78
1486877 9/1977 United Kingdom .

Primary Examiner—Hiram H. Bernstein
Attorney, Agent, or Firm—Sim & McBurney

[57] ABSTRACT

Wet chemical, microcomputer-controlled procedure for the rapid dissolution of metal followed by accurate determination of elements in the sample and, more specifically, suited to meet steel industry requirements for control of the level of acid-soluble aluminum in steel during the making of steel, is described. A sample of steel to be tested is normally placed in an electrolytic cell wherein a known portion of the sample is dissolved electrolytically in dilute cold acid. The aluminum content of the resulting solution is determined spectrophotometrically. The apparatus is compact and readily installed near the steelmaking operation.

15 Claims, 4 Drawing Figures

METAL ANALYSIS FOR ACID-SOLUBLE ELEMENTS

FIELD OF INVENTION

The present invention relates to the rapid dissolution of solid samples for the determination of one or more elements, and more particularly to a rapid procedure and reliable apparatus for the determination of the acid-soluble aluminum content of steel.

BACKGROUND TO THE INVENTION

During steelmaking, it is necessary to determine the amount of specific elements which influence the properties. Once this analysis has been made, the composition can be adjusted to meet the particular specification. In order to carry out the analysis, a sample of the steel is obtained using one of the many available techniques resulting in a solid form, usually disc-like. This sample may be analyzed by several procedures known to the art.

For rapid analysis, samples are usually prepared in the solid form by grinding a surface to a clean and flat condition and then analyzing the ground surface by a technique such as x-ray fluorescence (XRF) or optical emission (OE). In the case of certain elements which exist in steel, in both solid solution and compound form, the metallurgically-significant component is usually an acid-soluble component (hydrochloric, nitric or sulfuric acid are frequently used for solubilization). Aluminum is an example of such an element. Amongst other uses, aluminum is used for deoxidation of steel and the acid soluble aluminum content of steel provides a measure of the degree of deoxidation.

The prior art techniques of XRF and OE analysis suffer from the disadvantage that fundamentally they do not distinguish between the acid-soluble and acid-insoluble forms of elements and in fact they tend to respond more to the acid-insoluble form. In practice, therefore, supplementary methods for the determination of the acid-soluble fraction are necessary.

An alternative procedure which has been adopted is the determination of elements from an aqueous solution of sample. This procedure requires that fine drillings or millings from the steel sample are covered with strong acid and heated at close to boiling temperature for about 40 minutes until the steel sample is completely dissolved. Generally, the solution then must be brought to standard volume and acidity prior to analysis by a variety of techniques. The disadvantage of this method is that it generally takes too long for the results of analysis (by any method) to be available soon enough to be of value for process control, i.e., the adjusting of the composition of the steel to a specified range. Any attempt to shorten the time of dissolution by increasing the temperature and/or concentration of the acid may result in the partial dissolution of previously insoluble compounds. For example, in the case of the aluminum determination, the metallurgically-significant aluminum would be overestimated.

SUMMARY OF INVENTION

The present invention overcomes the difficulties of the prior art by utilizing the approach of quantitative electro-chemical dissolution of a small representative portion of the solid sample followed, sequentially, by the rapid quantitative determination of one or more elements in the solution. More specifically, in the case of the acid-soluble aluminum in steel, the analytical technique preferably used in this invention is the colorimetric method.

Accordingly, the present invention provides a method for rapidly determining the concentration of a variable concentration, usually minor constituent, acid-soluble material in a sample of an acid-soluble metal, which comprises: (1) coulometrically dissolving a predetermined amount of the acid-soluble metal from the sample to form a solution containing the predetermined amount of the acid-solubilized metal and also containing a variable amount of the variable concentration, acid-soluble material proportional to the amount thereof in the sample, and (2) analytically determining the amount of the variable concentration, acid-soluble element in the solution in relation to the predetermined amount of acid-soluble metal to provide a value proportional to the concentration of the variable concentration, acid-soluble material in the sample.

The variable concentration acid-soluble material usually is present in the sample in elemental form, but alternatively may be present in acid-soluble compound form. Usually it is variations in a relatively narrow range of a low concentration element in a sample which are of concern and the invention is described more particularly herein with reference thereto. However, the invention may be used for analysis for higher concentration materials, provided that proper calibration of the apparatus is effected prior to commencement of the coulometric dissolution of sample.

Further, while the invention is described hereinafter with particular reference to steelmaking and steel analysis, the principles of the invention may be applied to other acid-soluble metals and associated elements.

Some advantages of the approach of the present invention over prior techniques are that it provides the concentration of the minor constituent, acid-soluble element accurately and with sufficient speed for process control. More specifically, in the case of the acid-soluble aluminum determination in steel, the method is compatible with the existing sample form, the environment characteristic of control laboratories in steelmaking shops, and the speed and accuracy requirements of the steelmaking process. In addition, the apparatus which is utilized in the invention is relatively inexpensive and simple in construction.

The invention also includes a novel electrolytic cell construction for utilization in the electrolytic dissolution of metal in the above-described procedure. Such cell includes movably electrically-conductive mounting means for mounting a test sample into the cell and for moving the sample into and out of the cell through the open top. Spacing means is provided for spacing the sample a predetermined distance from an electrode fixedly located adjacent the bottom wall of the cell, when the sample is positioned by the mounting means adjacent the electrode to define a uniform gap therebetween. Pump means is located in the body for circulating aqueous acid solubilizing agent through the uniform gap between the electrodes while d.c. electrical current is applied between the electrodes across the gap.

GENERAL DESCRIPTION OF INVENTION

The coulometric dissolution of the substantially predetermined amount of the acid-soluble metal from a steel sample may be effected in any convenient manner. Usually, the coulometric dissolution is effected by contacting the steel sample with a small metered amount of acidic electrolyte recirculating in an electrolytic cell.

In such a cell, the steel sample is used as the anode and is spaced a small distance from an electrically-conductive cathode constructed of any convenient electro-conductive material, such as, platinum or graphite. A d.c. voltage is applied to the cell from an external power supply, resulting in current flow. The preferred arrangement is to use a constant current power source. Recirculation of the electrolyte between the electrodes permits the achievement of higher current densities and, as a consequence, quicker dissolution of the steel sample in a small volume of electrolyte.

The electrolyte, usually dilute hydrochloric acid, usually of normality from about 0.20 to about 0.50 N, is circulated through the gap between the sample (anode) and the platinum (cathode) to effect electrolytic dissolution of a predetermined portion of the steel sample, to replace electrolytic depletion of hydrogen ion and to purge gaseous by-product, which would otherwise inhibit efficient operation. The circulation preferably is effected by pumping the electrolyte through a central opening in the cathode into the gap, passing it radially through the gap in contact with the steel sample and then returning it to the pump. The purged gas is vented from the cell.

The cell and pump configuration are preferably designed to ensure that a small volume of electrolyte, such as about 18 to about 30 ml, is used. This permits the dissolution of a small quantity of steel sample while still achieving concentrations of elements in solution sufficient for accurate analysis. This feature enhances the rapidity of the method and the utility thereof for process control.

A novel feature of the invention is that the use of rapid electrolyte recirculation in conjunction with a very dilute acid electrolyte ensures the highest possible current density, hence the highest possible dissolution rate, commensurate with coulometric conditions being achieved, in that the amount of sample going into solution, for all practical purposes, obeys Faraday's Law. The time integral of current, i.e., the cross-product of current and time if the current is held constant, determines the amount of soluble sample which goes into solution. This permits either the calculation of the amount of the element in the steel sample directly from the measured concentration of the element in the solution or direct calibration in terms of the amount of the element in the sample.

Generally, ambient temperatures of about 15° to about 25° C. are utilized for the electrolytic dissolution of the metals, and hence the inaccuracies of the prior art which result from high temperature partial dissolution of aluminum compounds do not arise.

The electrolyte containing the acid soluble constituents of the steel sample may be drained from the cell into a reservoir and the concentration of acid-solubilized components determined.

The reservoir into which the cell is drained usually takes the form of a funnel, to permit residual solution to be drained efficiently after sampling. A filter paper or other filter medium may be placed in the funnel to filter out any acid-insoluble particulate residue which may have been released from the sample during electrolysis. The amount of such acid-insoluble residue collected in this way provides an indication of the cleanliness of the sample. The collected acid-insoluble residue may be subjected to an analytical procedure, if desired.

Analysis of the solution in the reservoir may be effected in any convenient manner, depending on the metal for which analysis is being made. For aluminum, the concentration is preferably determined colorimetrically. In such a procedure, a portion of the electrolyte is mixed with a suitable metallochromic indicator for aluminum and the absorbance of the resulting solution is measured at an appropriate wavelength. The measured absorbance is proportional to the aluminum concentration.

The overall procedure may be controlled by a microcomputer, so that an operator need only insert and remove the sample from the electrolytic cell and the result is calculated and displayed or recorded automatically.

DESCRIPTION OF PREFERRED EMBODIMENTS

Figure 1:
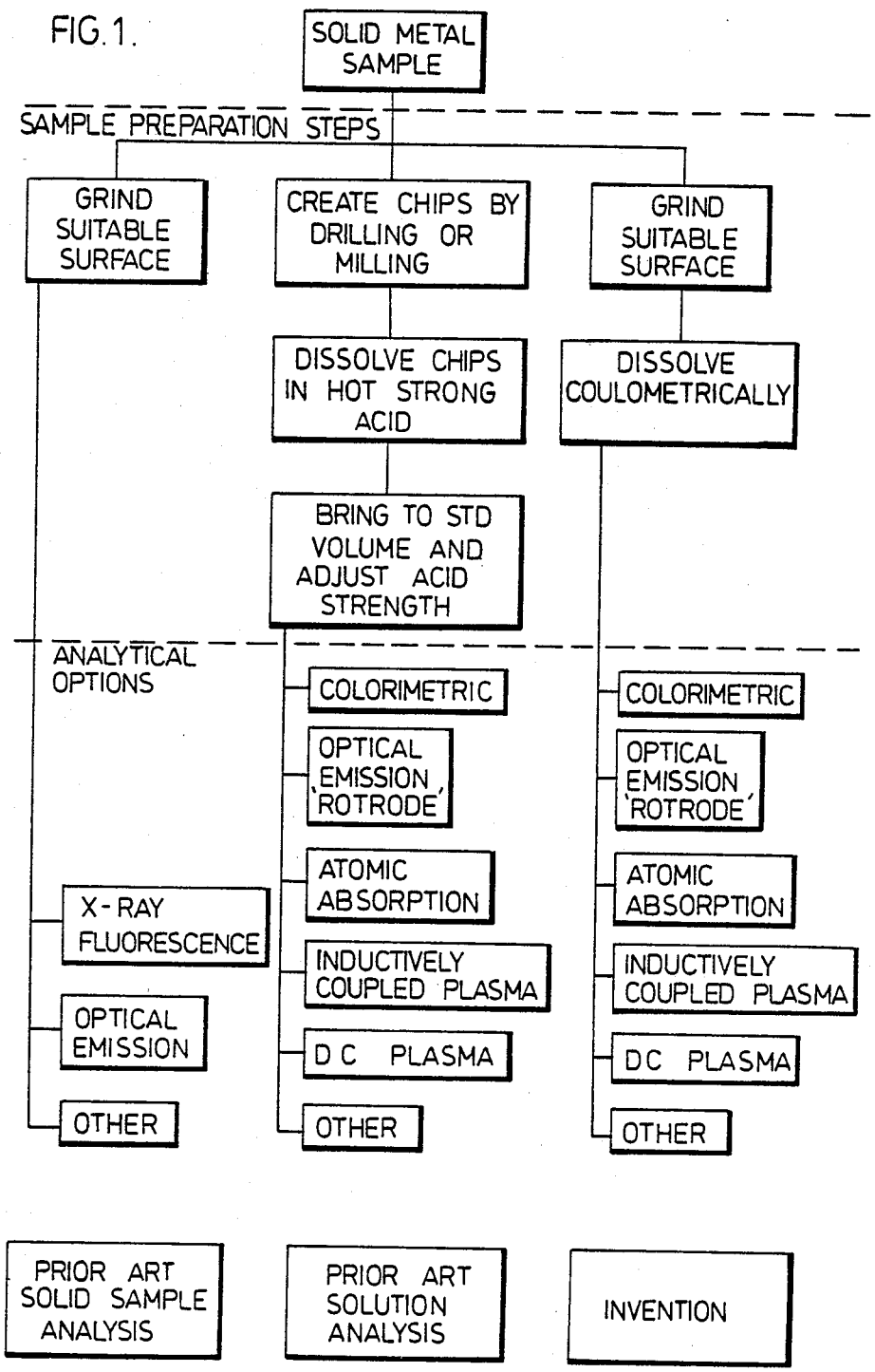
FIG. 1 is a schematic flow chart comparing the procedure of the present invention with typical prior art procedures.

Referring first to FIG. 1, there is illustrated schematically therein the procedure of the present invention in comparison with typical prior art operations. In each case, the procedure involves sample preparation steps and analysis.

As may be seen in FIG. 1, one prior art procedure involves grinding of a surface of the solid metal sample and then analysis of the ground surface by x-ray fluorescence, optical emission or otherwise. As mentioned above, this procedure is unsatisfactory since the analytical techniques cannot differentiate between acid-soluble and acid-insoluble forms of constituents of the sample.

Another prior art procedure involves the formation of drillings or millings from the sample, dissolution in strong acid and adjustment to standard volume and acid strength. Analysis of the solution may be effected by colorimetric, optical emission, atomic absorption, inductively coupled plasma, d.c. plasma or any other convenient technique. As mentioned previously, the major disadvantage of this prior art procedure is that the results of analysis usually are not received soon enough to be of value for process control.

As seen in FIG. 1, the process of the invention involves an initial grinding of a surface of the sample followed by coulometric dissolution of acid-soluble metals from the sample. The coulometric treatment rapidly dissolves a predetermined amount of the acid-soluble metal, e.g., iron, along with an amount of a minor constituent, acid-soluble element which corresponds to the proportion of that constituent in the sample. Analysis of the resulting solution by any convenient technique, such as, colorimetric, optical emission, atomic absorption, inductively-coupled plasma or d.c. plasma analysis, then determines the proportion of minor constituent element present in relation to the acid-soluble metal, thereby providing a determination of the concentration of the minor constituent element in the sample.

Since the coulometric dissolution and subsequent analysis can be effected rapidly and quantitatively in a total of less than about 5 minutes, normally less than about 3 minutes, the procedure can be used effectively for process control, enabling the composition of steel or other acid-soluble metal to be adjusted and maintained within a specified range of acid-soluble minor constituent element(s).

The contracts between the procedure of this invention and the prior art analytical procedures and the advantages which flow therefrom can be readily seen from FIG. 1 and the above description thereof.

Figure 2:
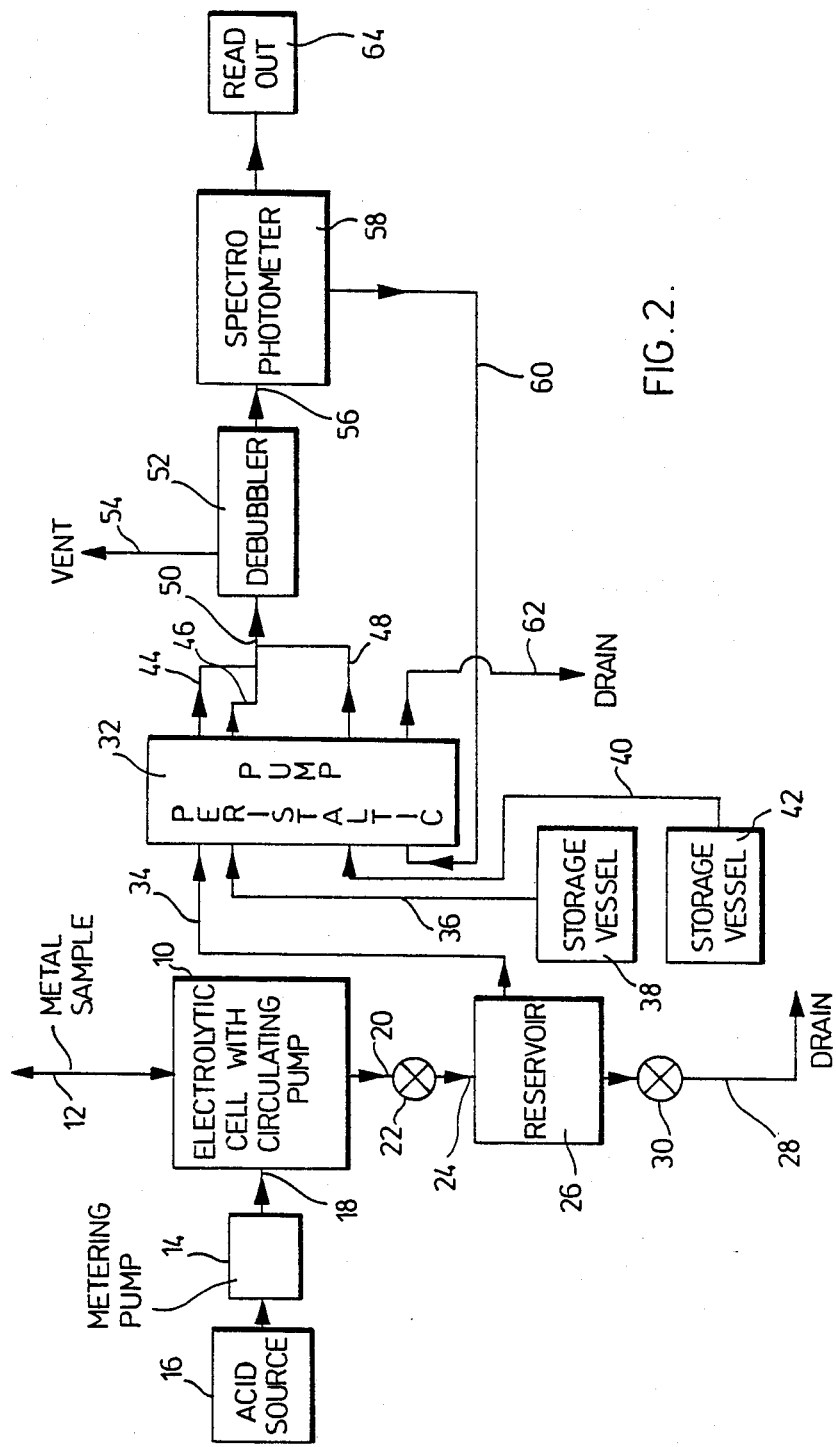
FIG. 2 is a schematic flow sheet of a rapid acid-soluble determination process and apparatus provided in accordance with a preferred embodiment of the invention.
Figure 3:
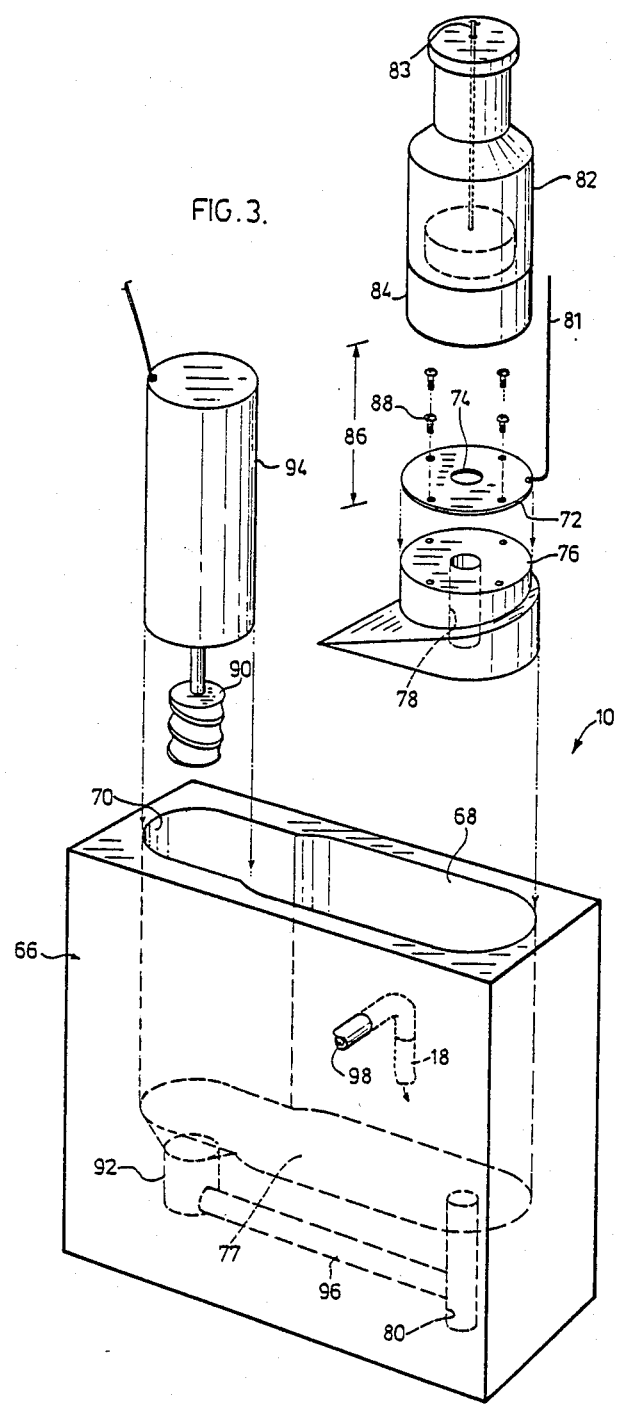
FIG. 3 is a perspective view of one embodiment of an electrolysis cell for use in the process and apparatus of FIG. 2.

Turning now to FIGS. 2 and 3, there is illustrated therein an apparatus for effecting the analytical technique of the invention. An electrolytic cell 10 receives a steel sample for analysis by line 12. The solid steel sample usually takes the form of a disc. Fresh hydrochloric acid at an ambient temperature of about 15° to about 25° C. is pumped by a metering pump 14 from an acid source 16 by line 18 into the cell 10. The hydrochloric acid provides a pool of electrolyte within the cell in which the cell electrodes, one of which is provided by the metal sample, are immersed. The hydrochloric acid is recirculated within the cell 10 by an internal pump.

A drain line 20 communicates with the electrolytic cell 10 to drain the hydrochloric acid from the cell 10 when desired. A solenoid valve 22 communicates with the lower end of the drain line 20 and normally closes the same against liquid flow out of the cell 10. Upon actuation of the solenoid valve 22, the liquor flows out of the cell 10, down the drain line 20, through the valve 22, through a further line 24 and into a reservoir 26.

The reservoir 26 is joined to a drain line 28 through a solenoid valve 30 which normally prevents flow from the reservoir 26 to the drain line 28 but may be selectively activated to permit such flow.

A peristaltic proportioning pump 32 is connected to the reservoir 26 by line 34. The pump 32 also is connected, by line 36, to a storage vessel 38 for a solution of a metallochromic indicator, and by line 40 to a storage vessel 42 for an ascorbic acid solution, which acts as an oxidation inhibitor.

The outlet lines 44, 46 and 48 from the peristaltic pump 32 corresponding to the inlet lines 34, 36 and 40 respectively merge to a single flow line 50, which is of a length to permit substantially maximum development of the absorbance to be measured to occur.

A debubbler 52 communicates with the downstream end of the flow line 50 to removed gas bubbles from the mixed streams, gases being vented by line 54. An inlet line 56 for a molecular absorption spectrophotometer 58 receives the debubbled liquid from the debubbler 52. The peristaltic pump 32 communicates with the outlet side of the spectrophotometer 58 by line 60 and pumps the liquid to drain by line 62.

The signal resulting from exposure of the liquid in the absorption cell of the spectrophotometer 58 to radiation and corresponding to the transmittance of the liquid is processed to a readout 64. For example, the signal may be passed to a microcomputer which determines the aluminum content of the metal sample from the value of the transmittance and displays the same on a video terminal fed by the microcomputer. When a microcomputer is used in this way, it may also be used to control the operation of various components of the system.

The rapid acid-soluble aluminum determination apparatus of FIG. 2 is compact and is readily installed adjacent the steelmaking operation, so that the aluminum content of the steel can be readily and rapidly determined, and adjusted, if necessary.

The detailed construction of the electrolytic cell 10 as shown in FIG. 3 now will be described. The cell 10 comprises a body 66 formed of any convenient corrosion-resistant material and having cavities 68 and 70 located therein contiguous with one another. A platinum disc electrode 72 having a central opening 74 is mounted on support member 76 located in the bottom of the cavity 68 in raised relation to the bottom wall 77 of the cavity to facilitate liquor flow. The support member 76 has a vertically-directed bore 78 therein which is aligned with the central opening 74 of the electrode 72 and also with a vertical bore 80 which extends through the bottom of the body 66, the bore 80 communicating with the drain line 20 (see FIG. 2). The platinum disc 72 is electrically-connected by a power lead 81 to a suitable d.c. power source.

A removable magnetic holder 82 is connected by a power lead 83 to the d.c. power source and is used to removably mount a disc-like steel sample 84 in the cell 10. The sample 84 is located by the holder 82 to be substantially coaxial with the platinum disc 72 and spaced therefrom to define a uniform gap 86 which forms an electrolysis zone between the sample 84 and the platinum disc 72. Non-conductive spacer elements 88 are used to maintain a predetermined dimension for the uniform gap 86, usually about 2 to about 3 mm.

A pump impeller element 90 is located in a recess 92 located at the bottom of the cavity 70 and is driven by a motor 94. The recess 92 defines a pumping chamber and is located below the level of the bottom wall 77 of the cavity 68. The recess 92 communicates with the bore 80 via a transverse bore 96 which extends between the two in the body 66 of the cell 10. Dilute hydrochloric acid, or other aqueous acidic solubilizing agent, is pumped by the impeller 90 from the recess 92 through the bore 96, the bore 80 and the bore 78 into the gap 86 between the platinum disc 72 and the sample 84. Pumped liquor flows back into the recess 92 under the influence of gravity. The transfer time from the gap 86 to the recess 92 should be sufficient to ensure complete separation of gas bubbles from the electrolyte.

The hydrochloric acid feed line 18 communicates with the interior of the cavity 68 through an opening 98 located in the side wall of the body 66.

OPERATION

In operation, the steel sample 84 is analyzed for acid-soluble aluminum content. The small steel disc, typically of diameter from about 20 to about 40 mm, first is ground both to remove any surface oxide scale and also to remove the immediate surface layer of the steel which may be depleted of acid-soluble aluminum, as a result of surface reactions with the air and confining surfaces. For proper functioning and accurate testing, it is essential to provide a clean flat surface of controlled area.

The sample disc 84, after surface grinding, is manually positioned in the cell 10 with the ground surface towards the platinum disc 72. A metered amount of dilute hydrochloric acid is then pumped into the cell 10 from the source 16 by metering pump 14 so as to enter the electrolysis zone 86 and wet the ground surface of the disc sample 84.

The pump motor 94 is started up to circulate the dilute hydrochloric acid pool through the orifice 74 in the platinum disc 72, radially through the electrolysis zone 86 and back to the impeller recess 92. The flow rate of the acid in the electrolysis zone 86 may vary widely provided that it permits electrolytic dissolution of metallic ions from the disc sample 84 and effects flushing of by-product gases. Usually the flow rate is in the range of about 400 to about 1000 ml/min.

Once the pump 94 is circulating the electrolyte, a constant current d.c. power is applied by a suitable power supply with the steel sample disc 84 being at a positive electrical potential and the platinum disc 72 being at a negative electrical potential. The current density applied should be sufficient to effect satisfactory electrolytic dissolution of metallic ions, and usually ranges from about 1.0 to about 2.5 amps/cm$^2$.

The reactions of primary interest pertaining to iron and aluminum and which occur at the amode, in acidic solution, may be represented as follows:

$$Fe \rightarrow Fe^{2+} + 2e^-$$

$$Al \rightarrow Al^{3+} + 3e^-$$

while, at the cathode, the reaction may be represented by the equation:

$$2H_2O + 2e^- \rightarrow H_2 + 2OH^-$$

The hydrogen which is evolved at the cathode pursuant to the latter equation is flushed away by the circulating dilute acid and does not interfere with the electrolytic dissolution of the steel sample. In the absence of such flushing, the ohmic voltage drop of the electrolyte would rise in proportion to the displacement of the electrolyte by the hydrogen evolved at the cathode and thereby severely limit the rate at which dissolution of the metallic species could occur at the amode. The flushed hydrogen vents from the cell 10, and hence is not recirculated by the pump 94.

Rapid circulation of the dilute acid not only removes evolved gases but also enables the initial acid concentration to be relatively low, since there is no chance for the electrolyte to become basic in the region of the amode as a result of the formation of a local high concentration of hydroxyl ion at the cathode. If the electrolyte were to become basic, then the reactions at the amode could be represented by the equations:

$$Fe + 2OH^- \rightarrow Fe(OH)_2 + 2e^-$$

$$Al + 4OH^- \rightarrow H_2AlO_3^- + H_2O + 3e^-$$

The ability to rapidly dissolve iron and aluminum from a steel sample using a non-oxidizing acid of low normality at ambient room temperature is of considerable importance in ensuring that an accurate determination of acid-insoluble aluminum has been effected. The low temperature and low acidity ensure that acid-soluble aluminum, such as the oxide or silicate, which are partly soluble in hot strong acids, especially upon extended exposure thereto, are not dissolved.

The anodic dissolution procedure which is effected in the electrolytic cell 10 puts into solution a weight of sample which is directly proportional to the time integral of current i.e., the cross product of current and time, if the current is held constant. The current of the cell and the external cell voltage are both monitored during the dissolution of the sample. Loss of circuit continuity, short circuit or out-of-limit cell voltage may be exhibited to the operator as an "alarm" condition, for example, on a video terminal.

Excessive scale on the back of the steel sample disc 84, corrosion products on the face of the magnet 82 or low level of electrolyte could cause an open circuit giving rise to the first type of alarm condition. A short circuit could be caused by the steel sample disc 84 touching the platinum disc 72 as a result of spacer failure or a steel silver bridging the electrolysis zone or gap 86, giving rise to the second type of alarm condition.

Under normal operating conditions, the cell voltage shows no short period fluctuations but rises very smoothly with time to reflect depletion of hydrogen ions in the electrolyte as electrolysis of the steel disc proceeds. Should the pump stall or slow down, the cell voltage fluctuates abnormally and rises above the expected value for that particular time of the cycle, giving rise to the third type of alarm condition. Termination of dissolution of the steel disc occurs when the cross-product of current and time reaches a preset value, usually after a period of about 15 to about 30 seconds.

Once the anodic dissolution of the steel disc is terminated, usually after a period of about 15 to about 30 seconds, the cell 10 is drained through drain line 24 by actuation of solenoid 22 into reservoir 26. The peristaltic proportioning pump 32 transfers the sample solution from the reservoir 26 by lines 34 and 44 to the inlet line 50 where it meets almost simultaneously the product of two other streams, namely indicator solution pumped by lines 36 and 46 from a storage vessel 38 containing any suitable aluminum metal indicator, such as the metallochromic indicator known as CHROME AZUROL-S, and containing a suitable buffer, such as, sodium acetate, and a solution of an oxidation inhibitor pumped by lines 40 and 48 from a storage vessel 42 containing any convenient ferrous ion oxidation inhibitor, such as, ascorbic acid.

The mixture is pumped through line 50 to develop absorbance to be measured in the molecular absorption spectrophotometer 58 and through the debubbler 52 to remove bubbles. The mixture enters the absorption cell of the molecular absorption spectrophotometer 58, before being pumped to drain line 62 through line 60. The length of the absorption cell depends on the make of the spectrophotometer 58, and is typically about 10 mm.

The sample in the absorption cell is exposed to radiation at a wavelength of 545 nm (characteristic of aluminum), thereby determining the concentration of aluminum in the sample.

When absorbance measurements have been completed, the reservoir 26 is drained to drain line 28 by actuation of the solenoid valve 30. Following drainage of the cell 10, the cell 10 is recharged with fresh dilute hydrochloric acid and the current passed in the reverse direction through the electrolytic zone 86 by reversal of the polarities of the sample 84 and the disc 72 for a short period of time to clean the platinum disc 72. The cell 10 is then again drained by line 20 by actuation of solenoid valve 22 to the receiving vessel 26, which itself is drained by drain line 28 by actuation of solenoid valve 30. The steel sample disc 84 is then removed manually from the cell.

The analytical procedure makes use of an automated solution analyzer approach which is conventionally operated in a continuous flow mode. However, in the above described operation, the apparatus operates in a controlled flow mode wherein the peristaltic pump 32 operates only when required to do so. A microcomputer may be programmed to exercise the peristaltic pump 32 periodically, even though no samples are being run, in order to avoid memory problems in flow rate regulation which may result from static pinching of the tubing by the rollers of the pump.

Other than to insert and remove the sample to be tested and to ensure an adequate chemical supply, the procedure may be free from manual involvement. A microcomputer may control the various operations, their sequence and the timing of each step.

SET-UP PROCEDURE

Before routine analysis of steel samples can be carried out following the above-described procedure, the instrumentation must be standardized to ensure accurate and consistant determinations of acid-soluble aluminum content of the steel samples. Similar standardization or calibration is effected for other samples.

A microcomputer may prompt the operator as to when to place a "Low ASA" steel standard in the cell 10 and when to place a "High ASA" steel standard in the cell 10. The computer has stored in its memory the expected values of percentage acid-soluble aluminum (% Al) for both of the reference materials.

The voltage measured by the spectrophotometer 58 for the "Low ASA", steel sample is considered to correspond to 0.000% Al and the computer program treats the voltage reading (V low) as if it corresponds to a transmittance of 100%. The voltage reading (V high) for the "High ASA" steel sample then is used to determine the value of the expression:

$$\log_{10}(V \text{ low})/(V \text{ high})$$

The ratio of this calculated net absorbance value to the expected value of % Al is used to normalize the routine results, prior to correction for non-linearity of the calibration curve relating net absorbance to % Al.

The calibration curve is derived from selected reference materials selected to cover the analytical range of 0.000 to 0.300% Al (acid-soluble aluminum).

The two-point standardization procedure described above compensates for batch-to-batch changes in the strength of the hydrochloric acid, the aging of the ascorbic acid, and/or the effectiveness of the metallochromic indicator.

Verification that the instrument is ready for routine analysis can be carried out at any time by running a midrange certified reference material and checking that the value determined is within the limits set for that material.

EXAMPLE

The apparatus of FIGS. 2 and 3 was set up and used to determine the acid-soluble aluminum content of a steel sample. A steel disc having a diameter of 32 mm and a thickness of 12 mm was spaced 4 mm from a platinum disc of 34 mm in diameter.

21 ml of an 0.225 N hydrochloric acid solution was pumped into the cell and power was applied across the electrodes from a d.c. voltage source of 24 volts open circuit with the current regulated to 12 amps, corresponding to a nominal current density of 1.5 amps/cm$^2$. The hydrochloric acid was circulated within the cell at a nominal flow rate between the electrodes of 500 ml/min.

Following completion of the electrolysis at 240 coulombs, the electrolyte was drained from the cell to the reservoir. Liquor was pumped from the reservoir to the spectrophotometer by the peristaltic pump at a rate of 2.05 ml/min along with 7.00 ml/min of Chrome Azurol-S indicator solution and 2.47 ml/min of ascorbic acid solution. The Chrome Azurol-S indicator solution contained 40 mg of Chrome Azurol-S and 540 mg of sodium acetate in 10 liters of solution. The ascorbic acid solution contained 160 g of ascorbic acid in 10 liters of solution. The sample was analyzed and the aluminum content of the original steel disc was determined to be 0.032 wt. %.

Figure 4:
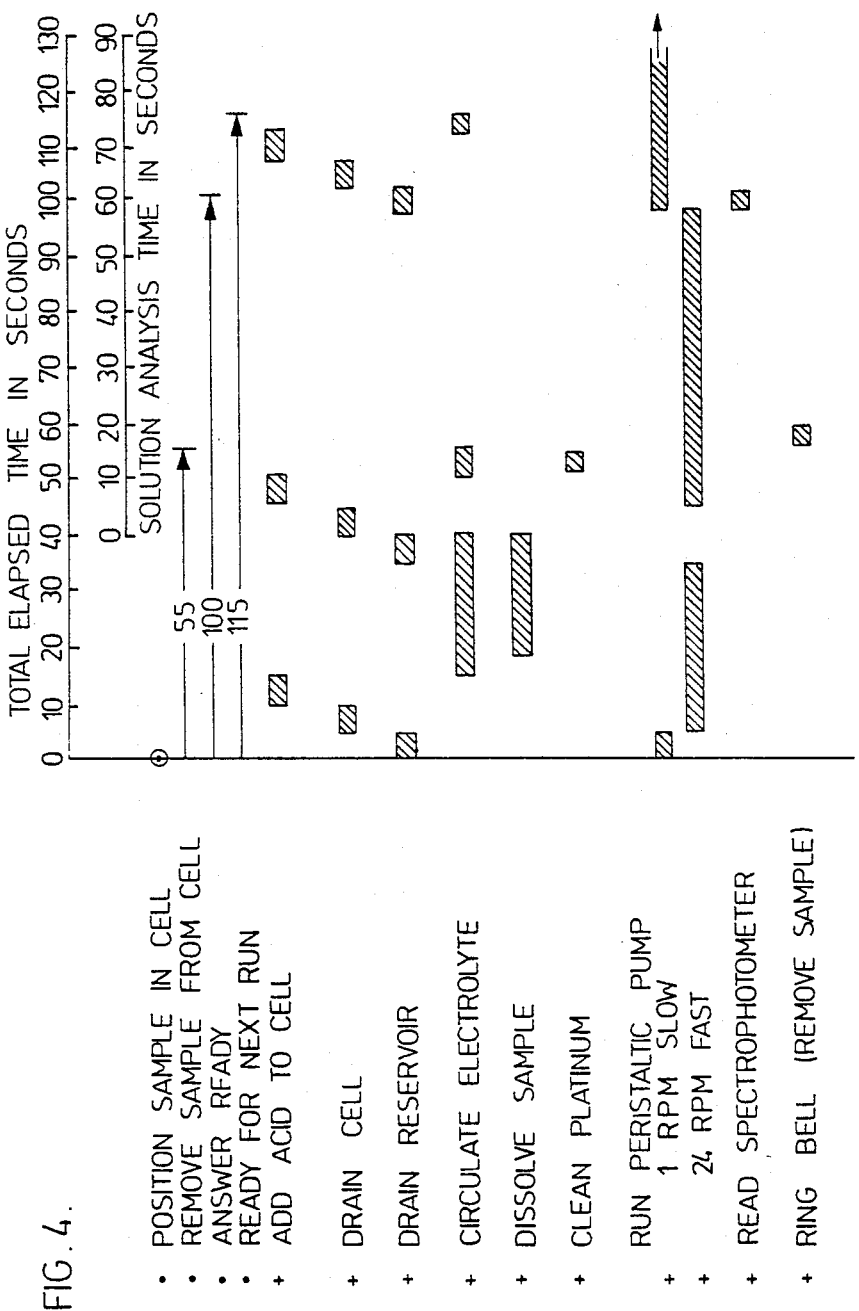
FIG. 4 is a typical timing chart for the various operations effected in the process and apparatus of FIG. 2.

The timing chart for the procedure of this Example appears as FIG. 4 of the drawings. Dissolution of the sample occurs in 20 seconds and the whole operation is complete in 115 seconds. The procedure, therefore, rapidly determined the aluminum content of the steel sample.

SUMMARY OF DISCLOSURE

In summary of this disclosure, there is provided a method for the rapid dissolution of a predetermined portion of a solid steel sample or other acid-soluble metal sample, in an aqueous acid solution for the purpose of quantitative determination of one or more elements in the solution. The invention has specific application to the accurate and rapid determination of the acid-soluble aluminum content of steel samples which arise in the making of steel. Modifications are possible within the scope of this invention. What I claim is:

1. A method for rapidly determining the concentration of a variable concentration acid-soluble material in a sample of an acid-soluble metal, which comprises:
   coulometrically dissolving a predetermined amount of said acid-soluble metal from said sample to form a solution containing said predetermined amount of acid-solubilized metal and also containing a variable amount of said variable concentration acid-soluble material proportional to the amount thereof in said sample,
   said coulometric dissolving being effected rapidly in an electrolytic cell containing a dilute aqueous solubilizing agent having a concentration insufficient to effect dissolution of the sample in the absence of electrolytic assistance by circulating the acidic solubilizing agent through an electrolysis zone between the sample acting as the amode electrode and the cell cathode to flush gaseous products of electrolysis from said electrolysis zone while maintaining high current density in the electrolysis zone during said coulometric dissolving, and
   analytically determining the amount of said variable concentration acid-soluble material in said solution in relation to said predetermined amount of metal to provide a value proportional to the concentration of said variable concentration acid-soluble material in said sample.

2. The method of claim 1, wherein said variable concentration acid-soluble material is an acid-soluble element which is present as a minor constituent in said sample.

3. The method of claim 2 wherein said sample is a steel sample and said minor constituent material is acid-soluble aluminum.

4. The method of claim 3 wherein said analytical determination is effected spectrophotometrically.

5. A method for the rapid dissolution of a known quantity of an acid-soluble metal from a test sample, which comprises:
providing an electrolytic cell containing an aqueous dilute acidic solubilizing agent for said acid-soluble metal and an electrode constructed of electroconductive material which is substantially inert to the solubilizing agent, said aqueous acidic solubilizing agent having a concentration insufficient to effect dissolution of said acid-soluble metal in the absence of electrolytic assistance,
positioning said test sample in spaced relationship with respect to said electrode to provide a substantially uniform gap therebetween to permit aqueous acidic solubilizing agent to be circulated therethrough and to define an electrolysis zone,
drawing aqueous acid solubilizing agent from a body thereof exterior to said cell into said electrolysis zone,
circulating said drawn agueous acidic solubilizing agent through, said gap between said test sample and said electrode and across the facing surfaces of said test sample and said electrode back into the body of acidic solubilizing agent while the sample is maintained at a positive potential and said electrode is maintained at a negative potential, whereby a d.c. current is applied therebetween, to effect contact between said circulating acidic solubilizing agent and said sample to electrolytically dissolve said metal in said electrolysis zone and to flush gaseous products of electrolysis from said electrolysis zone,
effecting separation of said flushed gaseous products of electrolysis from said body of acidic solubilizing agent exterior to said electrolysis zone,
continuing said acidic solubilizing agent recirculation through said gap and d.c. current application until a predetermined value of the integral of current overtime is attained based on dissolution of a predetermined amount of the metal from said sample by said agueous acidic solubilizing agent, and
thereafter removing from said electrolytic cell the aqueous acidifying agent containing the predetermined amount of the metal.

6. The method of claim 5 wherein said metal sample also contains a variable concentration of at least one additional acid-soluble material, whereby said removed agueous acidifying agent contains an amount of said at least one additional acid-soluble material proportional to the concentration thereof in said sample, and the amount of said at least one additional acid-soluble material present in the removed agueous acidifying agent is determined.

7. The method of claim 5 wherein said metal sample is steel.

8. The method of claim 6 or 7 wherein said at least one additional acid-soluble material is acid-soluble aluminum present in a minor proportion in said sample.

9. The method of claim 8 effected periodically to achieve process control in steelmaking.

10. The method of claim 8 wherein said acid-soluble aluminum content is determined spectrophotometrically.

11. The method of claim 10 wherein said spectrophotometric determination is effected by:
mixing said spent aqueous acidifying agent with a metallochromic indicator for aluminum, and
measuring the absorbance of the resulting liquid.

12. The method of claim 8 wherein said aqueous acidifying agent is dilute hydrochloric acid of normality from about 0.2 to about 0.5 N, the electrolysis is effected at an ambient temperature of about 15° to about 25° C., said aqueous acidifying agent is recirculated through said electroylsis zone at a flow rate of about 400 to about 1000 ml/min, and a current density of about 1.0 to about 2.5 amps/cm$^2$ is applied across said electrolysis zone.

13. The method of claim 12, wherein said electrolysis is effected for about 15 to about 30 seconds.

14. The method of claim 5 wherein said circulating solubilizing agent enters the electrolysis zone axially of the electrode and passes radially through the electrolysis zone.

15. The method of claim 5 wherein said removed aqueous acidifying agent is filtered to remove therefrom acid-insoluble particulates which have been removed from said sample during said electrolysis.

* * * * *